(12) United States Patent
Finke

(10) Patent No.: US 12,376,975 B2
(45) Date of Patent: Aug. 5, 2025

(54) ORTHOPEDIC DEVICE

(71) Applicant: Ottobock SE & Co. KGAA, Duderstadt (DE)

(72) Inventor: Lars Benjamin Finke, Landolfshausen (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 167 days.

(21) Appl. No.: 17/311,666

(22) PCT Filed: Dec. 2, 2019

(86) PCT No.: PCT/EP2019/083246
§ 371 (c)(1),
(2) Date: Jun. 7, 2021

(87) PCT Pub. No.: WO2020/120187
PCT Pub. Date: Jun. 18, 2020

(65) Prior Publication Data
US 2022/0104954 A1    Apr. 7, 2022

(30) Foreign Application Priority Data

Dec. 10, 2018 (DE) ............ 102018131550.3

(51) Int. Cl.
*A61F 2/80*    (2006.01)
*A61F 2/78*    (2006.01)

(52) U.S. Cl.
CPC .............. *A61F 2/7812* (2013.01); *A61F 2/80* (2013.01); *A61F 2002/7806* (2013.01); *A61F 2002/7837* (2013.01); *A61F 2002/802* (2013.01)

(58) Field of Classification Search
CPC .... A61F 2/7812; A61F 2/80; A61F 2002/802; A61F 2/7843; A61F 2002/807;
(Continued)

(56) References Cited

U.S. PATENT DOCUMENTS 5,156,629 A * 10/1992 Shane ............... A61F 2/80
                                                 128/DIG. 20
5,387,245 A *  2/1995 Fay ................. A61F 2/7843
                                                 623/901

(Continued)

FOREIGN PATENT DOCUMENTS

CN    106667629 B    4/2018
DE       917687 C    9/1954
(Continued)

OTHER PUBLICATIONS

First Search Report dated Jul. 29, 2023; Chinese Patent Application No. 201980077192.7; 10 pages.
(Continued)

*Primary Examiner* — Seema Mathew
(74) *Attorney, Agent, or Firm* — HOLLAND & HART LLP

(57) ABSTRACT

The invention relates to an orthopedic device comprising a main part with a first surface which is provided with at least one adhesive region. At least one recess is provided in the main part, said at least one recess being at least partly formed behind the adhesive region and being provided with a pressure and/or suction connection. The first surface is designed to be at least partly suctioned into the recess when negative pressure is applied in the at least one recess and or pushed out when positive pressure is applied.

19 Claims, 2 Drawing Sheets

(58) Field of Classification Search
CPC ...... A61F 2005/0172; A61F 2007/0239; A61F 2/78; A61F 2/54; A61F 2/50; A61F 2/60; A61F 2/602; A61F 2002/7818; A61F 2002/7837; A61F 2002/607; A61F 2002/608; A61F 2/0077; A61F 2002/3007; A61F 2002/501; A61F 2250/0021; A61F 5/0102; A61F 5/01; A61F 2002/7806

See application file for complete search history.

(56) References Cited

U.S. PATENT DOCUMENTS

| | | | | |
|---|---|---|---|---|
| 11,173,057 | B2* | 11/2021 | Smith | A61F 2/80 |
| 11,622,870 | B1* | 4/2023 | Johnson | A61F 2/64 |
| | | | | 623/32 |
| 11,969,366 | B2* | 4/2024 | Egilsson | A61L 27/56 |
| 12,036,137 | B2* | 7/2024 | Størup | A61F 2/80 |
| 12,042,408 | B2* | 7/2024 | Redkar | A61F 2/70 |
| 2002/0128580 | A1* | 9/2002 | Carlson | A61F 5/01 |
| | | | | 602/54 |
| 2003/0078674 | A1* | 4/2003 | Phillips | A61F 2/7843 |
| | | | | 623/56 |
| 2004/0122528 | A1* | 6/2004 | Egilsson | A61F 2/7812 |
| | | | | 623/36 |
| 2004/0143345 | A1* | 7/2004 | Caspers | A61F 2/80 |
| | | | | 623/36 |
| 2010/0070051 | A1* | 3/2010 | Carstens | A61F 2/80 |
| | | | | 623/36 |
| 2010/0318195 | A1* | 12/2010 | Kettwig | A61B 5/25 |
| | | | | 623/36 |
| 2016/0206448 | A1* | 7/2016 | Klutts | A61F 5/01 |
| 2018/0036151 | A1* | 2/2018 | Garus | A61F 2/5046 |
| 2018/0185176 | A1 | 7/2018 | Jonsson | |
| 2019/0038439 | A1 | 2/2019 | Caspers | |
| 2021/0100664 | A1* | 4/2021 | Jackson | A61F 2/7812 |

FOREIGN PATENT DOCUMENTS

| | | | |
|---|---|---|---|
| DE | 102014011373 A1 | 2/2016 | |
| EP | 2735290 A1 | 5/2014 | |
| EP | 3100704 A1 | 12/2016 | |
| KR | 20090019051 A * | 2/2009 | ........... A61F 2/7812 |
| WO | 2013033669 A2 | 3/2012 | |

OTHER PUBLICATIONS

International Search Report issued in International Application No. PCT/US2019/083246 on Mar. 10, 2020, 2 pgs.

* cited by examiner

ORTHOPEDIC DEVICE

CROSS-REFERENCE TO RELATED APPLICATIONS

This is a national phase application of International Application No. PCT/EP2019/083246, filed 2 Dec. 2019, which claims the benefit of German Patent Application No. 102018131550.3, filed 10 Dec. 2018, the disclosures of which are incorporated, in their entireties, by this reference.

TECHNICAL FIELD

The invention relates to an orthopedic device comprising a main body with a first surface which is provided with at least one adhesive region. The first surface can be of a closed design.

BACKGROUND

Orthopedic devices are often arranged on a user in order to provide the latter with support or to form an interface or a contact point on which further components can be arranged. For example, cuffs can be placed around a limb in order to support the muscles or joints. Moreover, the prior art includes what are called liners, which are pulled over a stump in order to allow protection of the stump against pressure points. A dimensionally stable socket, on which further prosthesis components are arranged, is arranged on the outer face of the liner. There are also so-called knee sleeves serving as sealing elements, which are applied to the outer face of a prosthesis socket, cover the proximal edge and provide a seal in order to generate a negative pressure.

The inner face of such an orthopedic device is in many cases provided with an adhesive surface or is provided at least in some regions with an adhesive surface in order to maintain the respective orthopedic device in as stable a position as possible. The inner face can either bear directly on the limb and prevent slipping or sliding of the orthopedic device on the limb, or it can bear on a further orthopedic component, for example on the outer face or an inner face of a prosthetic or orthotic device, for example if the orthopedic device is designed as a liner or inner socket between a stump and a prosthesis socket. Adhesive surfaces can be arranged both on the inner face and on the outer face of the orthopedic device in order, by means of corresponding retaining forces, to prevent or reduce a relative movement of the orthopedic component arranged on the outer face, for example the prosthesis socket, and the stump.

The adhesive forces described are deliberately applied in order to avoid relative movements. However, they make it considerably more difficult to fit an orthopedic component in place. The process of fitting an orthopedic component in place requires relative movements of the orthopedic component in order to position the latter in the intended manner on the body of the user. Since the formation of adhesive surfaces is essential for achieving the desired function, namely that of avoiding a change of position, for example in order to avoid loss or slipping of a prosthesis during walking, the awkward task of fitting and removing a liner is accepted. The technique of rolling on and unrolling the liner was developed for this purpose. This method does not permit subsequent corrections, or permits them only to a slight extent, and therefore a correction requires the entire liner to be unrolled and then rolled back on again.

Similar problems exist in other areas of use of orthopedic devices.

The object of the present invention is to make available an orthopedic device that is easy to fit in place, without its functionality being limited.

SUMMARY

According to the invention, this object is achieved by an orthopedic device having the features of the main claim. Advantageous embodiments and developments of the invention are disclosed in the dependent claims, the description and the figures.

In the orthopedic device comprising a main body with a first surface which is provided with at least one adhesive region, provision is made that at least one recess is present in the main body, said at least one recess being at least partially formed behind the adhesive region and being provided with or coupled to a pressure and/or suction port, wherein the first surface is designed in such a way as to be at least partially sucked into the recess when a negative pressure is applied in the at least one recess and/or to be pushed out when a positive pressure is applied. The inward sucking of at least parts of the first surface has the effect that the sucked-in parts or regions are no longer in contact with, for example, the skin surface, a socket inner face or another surface, such that in this region no adhesive surface portions bear directly on the other surface. The adhesive region is thus removed from contact with the other surface, such that the adhesive action of the orthopedic device decreases overall. Alternatively or in addition, it is possible, by applying a positive pressure, to push out the adhesive region and have it protrude beyond the plane of the first surface without positive pressure. It is thereby possible to set and switch between different adhesion conditions. If a vacuum is applied, the orthopedic device, as a result of the reduced adhesive surface area, can be easily pulled or pushed along another surface, for example in order to be able to fit the orthopedic device over a stump, over a body part or another orthopedic component, for example a prosthesis socket. If, for example, the adhesive regions are designed set back and are shaped like hollows, the orthopedic device can be easily fitted in place and corrected in terms of position without positive pressure, and, after application of a positive pressure, it bears firmly on the respective surface and adheres thereto. Both effects can also be combined: a negative pressure for fitting in place, and a positive pressure for increasing the adhesive forces. This is particularly advantageous in the case of orthopedic devices which are intended to be placed fully circumferentially around another orthopedic device or around a limb or are intended to be pushed into a receptacle, for example into a circumferentially closed prosthesis socket.

In a variant of the invention, provision is made that the first surface is designed separately from the main body and is secured thereon. It is thereby possible to easily introduce the recesses inside the main body, for example by cutting out or during the primary forming. It is thus possible, for example, that bores, continuous slits or channels or also individual depressions are introduced or arranged on a surface of the main body and are then covered by the first surface after the first surface has been connected to the main body. In this way, a channel system, or a system of interconnected recesses such as depressions, can be easily produced, which system can be evacuated or provided with positive pressure and can thus be designed to be switchable in terms of the adhesive regions.

The introduced recesses or passages and channels are preferably coupled to the pressure and/or suction port. In the case of continuous recesses or slits, the side or surface of the main body lying opposite the first surface can be covered by a further, separate surface, for example a coating or an applied cover in the form of a film or the like, in order to permit a negative pressure or positive pressure. The cover is impermeable to air or substantially impermeable to air, in order to allow the first surface to be sucked into the recesses, and, on a side of the main body lying opposite the first surface, is secured on the main body as a second, separate surface which at least covers the recesses.

As an alternative to a multi-part design of the orthopedic device, there is the possibility of forming the main body and the first surface together, for example in the context of an additive manufacturing method, for example 3D printing or a similar method, by which it is possible to form both a closed surface and also recesses which lie behind the latter and which can be evacuated via a suction port or can be inflated via a pressure port.

In a development of the invention, provision is made that the entire first surface is designed to be adhesive, such that, by being simply pulled back and brought out of contact after the evacuation of the recesses, a sufficient reduction in adhesion takes place to permit a movement of the orthopedic device relative to a limb or another component. As an alternative to an adhesive design over the full surface, for example with a suitable material of the first surface that can be formed as a film or mat, for example of silicone, there is the possibility of a coating that reduces the basic adhesion being applied to some regions of the first surface. For example, by applying a parylene coating, an adhesion-reduced or slippery surface can be applied for example in the context of a CVD process, such that, after the first surface has been pulled back or sucked into the recesses, there is no longer an adhesive surface within the plane which, without positive pressure or evacuation of the recesses, is formed by the first surface. If the coating, without a change of pressure in its starting state, is not located in a contact plane, the contact can be produced and adhesion effected by a positive pressure.

The adhesive action of the adhesive regions can be achieved in particular by an adhesive material, coatings or surface structuring. In a development of the invention, the adhesive action can be achieved or supported by a form-fit engagement; the adhesive regions can thus provide a hook-and-loop arrangement for example and, by application of a positive pressure, can be pressed against a corresponding mating piece, which can be secured for example on the inner face of a socket. The adhesive action can also be strengthened or weakened by the surface structuring of the adhesive region and suitable structuring of the contact surface, for example on the inner face of a socket.

As an alternative to the coating with an adhesion-reducing material, there is the possibility that the first surface is provided with an adhesion-strengthening coating in those regions that are present above the recesses. For example, an adhesive coating of silicone or the like can be applied above the recesses in order to ensure increased positional stability in these regions and to prevent or reduce a movement relative to further components or a limb. The adhesive coating and/or the adhesive region of the surface can correspond to the recesses or can be smaller or can also extend over the recesses.

In a variant of the invention, provision is made that a plurality of cup-like or channel-shaped recesses are arranged or formed in the main body and are fluidically connected to the pressure and/or suction port. It is thereby possible, for example, for fully circumferential regions with increased adhesion to be brought into or out of contact or for large surface areas of the orthopedic device to be provided with different adhesion properties.

In a development of the invention, provision is made that at least one or more of the cup-like or channel-shaped recesses in the main body are fluidically connected to the pressure and/or suction port via at least one valve, such that a pumping or suctioning operation does not have to take place permanently, and instead a vacuum, once established, or a negative pressure or positive pressure, once established, is maintained in the recesses. This is particularly the case when the valve is designed as a non-return valve. The valve is preferably switchable, such that it is also possible for the evacuated recesses to be filled with a medium, in particular ambient air, in order to achieve an increase in adhesion or, conversely, to release the positive pressure from the recesses.

If a plurality of cup-like or channel-shaped recesses are arranged in the main body, they can preferably be fluidically connected to one another, such that only one pressure and/or suction port is needed to evacuate the recesses and channels or to provide them with a negative pressure or positive pressure. Throttles or valves can be arranged between the fluidically interconnected recesses, in order to be able to adjust or control the respective pressure level inside the recesses. The valves can be adjustable or switchable, in order to be able to form regions with different pressures in the recesses in the orthopedic device. It is also possible to provide a plurality of pressure and/or suction ports for different recesses.

In a development of the invention, provision is made that the recesses extend as far as an edge of the orthopedic device in order to prevent a situation where, after an orthopedic device has been fitted in place and evacuation has taken place, a suction effect occurs and, for example, part of the skin is also sucked into the recess.

In a development of the invention, provision is made that the first surface is produced from an elastic material, such that, after removal of a vacuum, there is the possibility that the first surface returns to the starting position on account of the restoring force of the material, such that a substantially flat surface or a surface provided with indents is formed by the first surface when a vacuum or negative pressure or positive pressure is not applied.

In a development of the invention, provision is made that the orthopedic device is designed as a cuff, prosthesis liner, prosthesis socket or prosthesis socket component. Particularly in an embodiment as a cuff, prosthesis liner or prosthesis socket to be fitted circumferentially, fitting is made easy by the evacuation and the disengagement of the adhesive regions, without a relative movement of the orthopedic device on the limb being permitted after removal of the vacuum. Alternatively, access is possible at normal pressure in the case of adhesive regions that are set back, and a relative movement is prevented at positive pressure when adhesive regions are in active contact. In an embodiment of the orthopedic device as a prosthesis socket component, fastening devices for reversible fastening to a dimensionally stable outer socket are provided in one development, such that the prosthesis socket component can be designed as a flexible and optionally elastic inner socket, which is reversibly fastenable inside a rigid outer socket. With the switchable adhesion reduction and switchable adhesion increase through evacuation or filling of the recesses, it is possible, without removing the prosthesis socket component, to provide a rigid outer socket with a padding into and out of which the stump can be easily inserted and removed, respectively, and which at the same time bears in a stable position on the limb during use. The fastening devices serve for the replacement and optionally the cleaning of the prosthesis socket component in the form of an inner socket, in order to be able to easily clean the latter. Correspondingly, a prosthesis liner can also easily be brought into engagement with a dimensionally stable outer socket in order to secure the outer socket to the patient.

BRIEF DESCRIPTION OF THE DRAWINGS

An illustrative embodiment of the invention is explained in more detail below with reference to the attached figures, in which.

DETAILED DESCRIPTION

Figure 1:
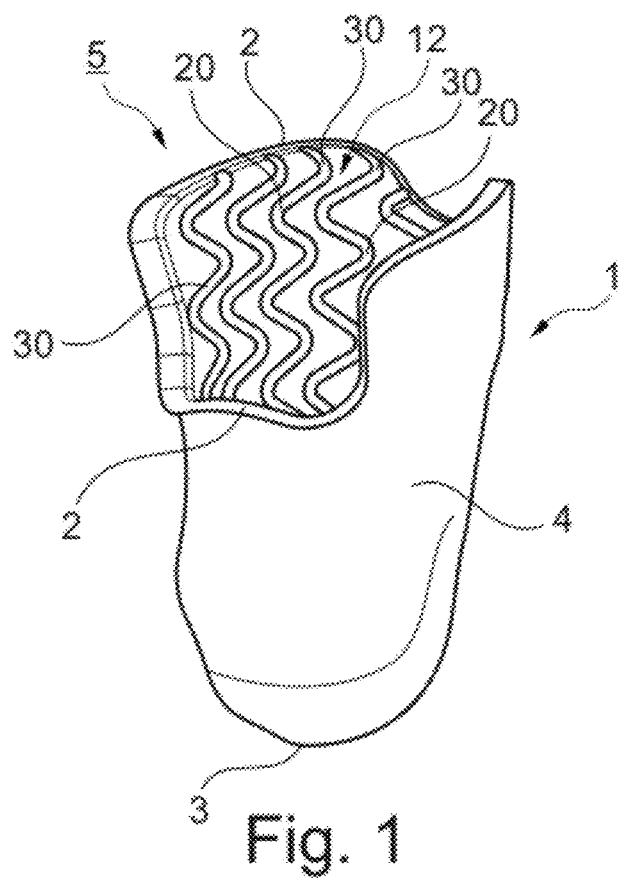
FIG. 1 shows a perspective view of a prosthesis socket.

FIG. 1 shows a perspective overall view of a prosthesis socket 1 with a dimensionally stable outer shell 4 which forms a proximal access opening 5 surrounded by a proximal edge 2. The prosthesis socket 1 forms a distal, closed end region 3 on which fastening devices (not shown) for a further, distal prosthesis component are arranged. The distal prosthesis component can be a functional unit such as a prosthetic foot or a prosthetic hand or, in another embodiment, a prosthetic joint. The prosthesis socket 1 in the illustrative embodiment shown is a lower-leg socket that can be fitted on a lower-leg stump.

On the inner face of the prosthesis socket 1, an orthopedic device is arranged which is either connected permanently to the dimensionally stable outer socket 4, for example welded, adhesively bonded or otherwise secured thereon, or designed with same, or is fastened releasably thereto via fastening devices or fastening elements. The orthopedic device would then be part of the prosthesis socket and would be designed as a prosthesis socket component which on the inner face, i.e. on the side directed toward the limb stump, has a first surface 12 provided with at least one adhesive region 20. In the illustrative embodiment shown, a plurality of regions 20 distributed about the whole circumference are arranged in zigzag lines from the proximal edge 2 as far as the distal end region. Other forms are likewise possible. In particular, straight lines or lines arranged in a spiral shape can likewise be arranged or formed on the first surface 12. Behind the adhesive regions 20, channels 30 are worked out inside a main body, which will be explained later. The channels 30 are connected by a pressure and/or suction port (not shown) to a pump or a compressor via which air can be pumped into the channels 30 or via which air can be pumped out of the channels 30. The port for a pump or a compressor can be arranged on the stable outer socket 4 or on the orthopedic device on the inner face of the outer socket 4.

Figure 2:
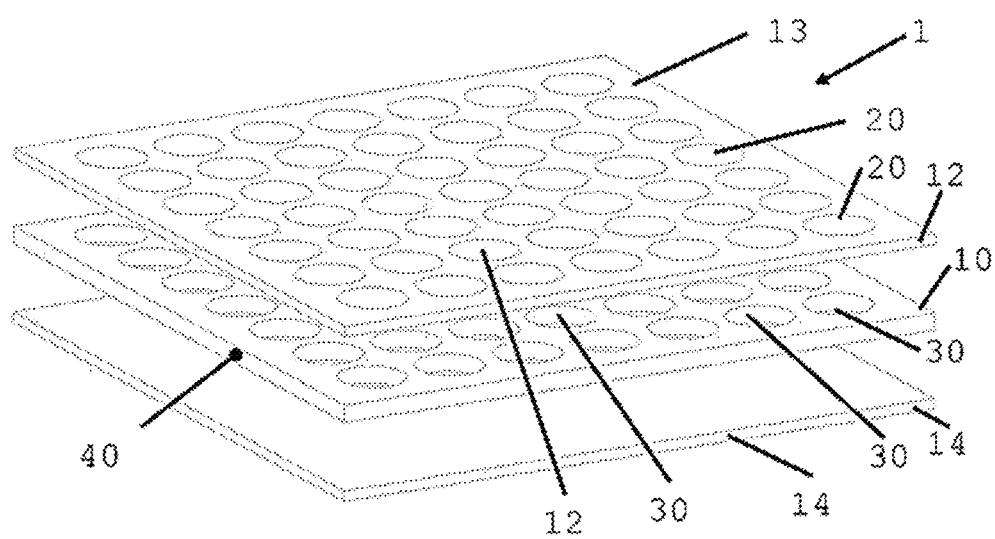
FIG. 2 shows an exploded view of a first embodiment.

FIG. 2 shows a perspective exploded view of an orthopedic device 1 with a main body 10 which is preferably flexible, in particular elastic, and with a first surface 12 and a second surface 14. The first and second surfaces 12, 14 are designed as films or layers of a suitable material, for example silicone or another polymer. Both the main body 10 and the two surfaces 12, 14 can have a predefined shape, which is substantially maintained when the orthopedic device 1 is in use. In the illustrative embodiment shown, the orthopedic device 1 is designed as a planar element which, for example, can be arranged on the inner face of a prosthesis socket and can be fastened thereon permanently or reversibly. There is also the possibility of the second surface 14 being formed by the prosthesis socket or another component.

A port 40 for a suction and/or pressure device, i.e. a pump and/or a compressor, is arranged or formed on the main body 10 in order to pump air or a fluid out of recesses 30 in the main body 10 or to pump a fluid into them. In the illustrative embodiment shown, the recesses 30 are designed as through-holes; they can be formed during the process of production of the main body 10 or can be introduced later, for example by being punched out, by being cut out or by other separating methods. To produce the orthopedic device 1, the main body 10 is connected to the second surface 14 on the underside or outer side of the main body 10, for example by welding or adhesive bonding, such that a substantially closed outer surface is obtained. On the opposite side of the main body 10, the first surface 12 is applied likewise in such a way that an airtight connection to the main body 10 is present, for example by means of a weld seam or adhesive seam running about the circumference or surrounding the recesses 30. The individual recesses 30 can be fluidically connected to one another by connection channels. These connection channels can be formed in the main body 10, in the second surface 14 or in the first surface 12, and it is likewise possible to form a plurality of fluidic connections, such that the volumes formed in each case by the first surface 12, by the main body 10 with the recesses 30 and by the second surface 14 can be evacuated and/or filled with a fluid.

On the upper side of the first surface 12, i.e. on the side lying opposite the main body 10, adhesive regions 20 are formed, which are arranged corresponding to the recesses 30 in the main body. In the illustrative embodiment shown, the recesses 30 and also the adhesive regions 20 are round. The surface area or extent of the adhesive regions 20 corresponds substantially to the contour of the recesses 30. In principle, it is also possible that the surface area of the adhesive regions 20 is smaller or also slightly greater than the surface area of the recesses 30 lying underneath. Beyond the adhesive regions 20, the surface 12 on the inner face is smoother or less adhesive, in particular being provided with a coating 13 that reduces adhesion. The inner face or upper side of the first surface 12 can initially be produced from an adhesive material, for example an adhesive silicone, which by means of a corresponding coating, for example by means of a parylene coating in the context of a CVD process, is divided into adhesive regions 20 separated from one another. Conversely, there is the possibility of initially producing the surface 12 from a smooth, non-adhesive material and then applying the adhesive regions 20 by a corresponding coating.

In the illustrative embodiment shown in FIG. 2, the main body 10 and the two surfaces 12, 14 are each formed as separate structural parts or components which are fastened to one another in order to form a cavity together with the recesses 30. This has the advantage of being a simple manufacturing method permitting a high degree of variability in production.

In the illustrative embodiment shown, the adhesive regions 20, and the regions of the inner face of the first surface 12 that are provided with an adhesion-reducing coating 13, are situated in a common plane. When a negative pressure is applied via the suction port 40, the regions of the first surface 12 that lie above the recesses 30 are sucked into the recesses 30. If the second surface 14 is more dimensionally stable than the first surface 12, only the material of the first surface 12 is sucked into the recesses 30. In this way, the adhesive regions 20 are brought into a plane which lies deeper than the starting plane or the plane of the adhesion-reducing coating 13 or below the plane of the material of the main body, such that the adhesive regions 20 no longer bear, or bear only to a reduced extent, on a body coming into contact with the side of the first surface directed away from the main body. It is thereby possible to adjust the friction between the orthopedic device 1 and the body by application of a negative pressure. Conversely, by application of a positive pressure by pumping fluid in through the pressure port 40, the adhesive regions 20 can be pressed out such that they protrude beyond the base plane, in order thereby to bring exclusively the adhesive regions 20 into contact or to permit an increased contact pressure of the adhesive regions 20 on the body. In principle, it is also possible to initially provide set-back adhesive regions 20, i.e. hollow-like or cup-like adhesive surfaces remaining behind the base plane, which only by application of a positive pressure in the recesses come into contact with a body lying or bearing thereon. The material of the first surface 12 is preferably elastic or provided with a restoring ability, such that the first surface 12 returns to a starting position after removal of a positive pressure or negative pressure.

Figure 3:
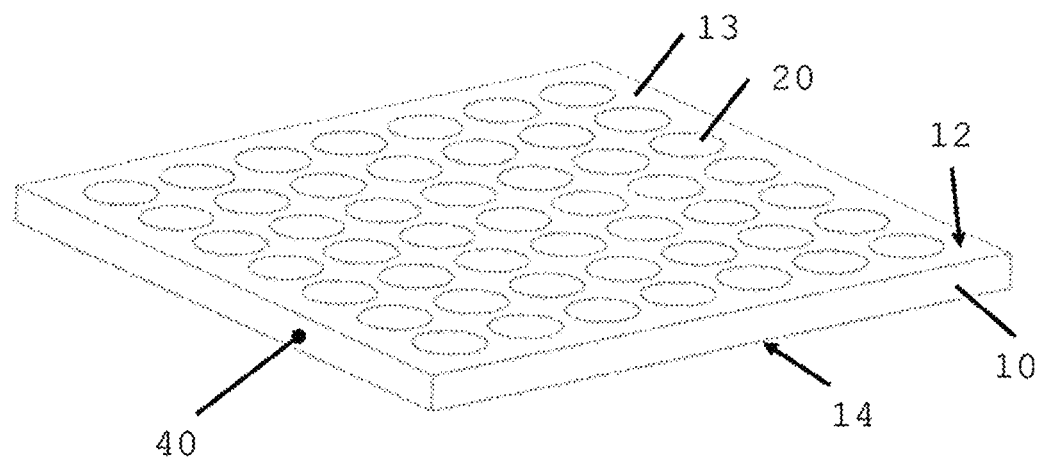
FIG. 3 shows a variant of the invention in the starting state.

A variant of the invention is shown in FIG. 3 in which, instead of a multi-part embodiment of the orthopedic device 1 with a separate main body 10, a separate first surface 12 and a separate second surface 14, a one-piece design is chosen. The method of producing an orthopedic device of this kind can for example have additive components such that, in the production of the orthopedic device 1, the recesses in the form of cavities and also their fluidic connections and the adhesive regions 20 can be generated during the primary forming method. In FIG. 3, the orthopedic device 1 is shown in a starting state in which the upper side of the first surface 12 is substantially flat.

Figure 4:
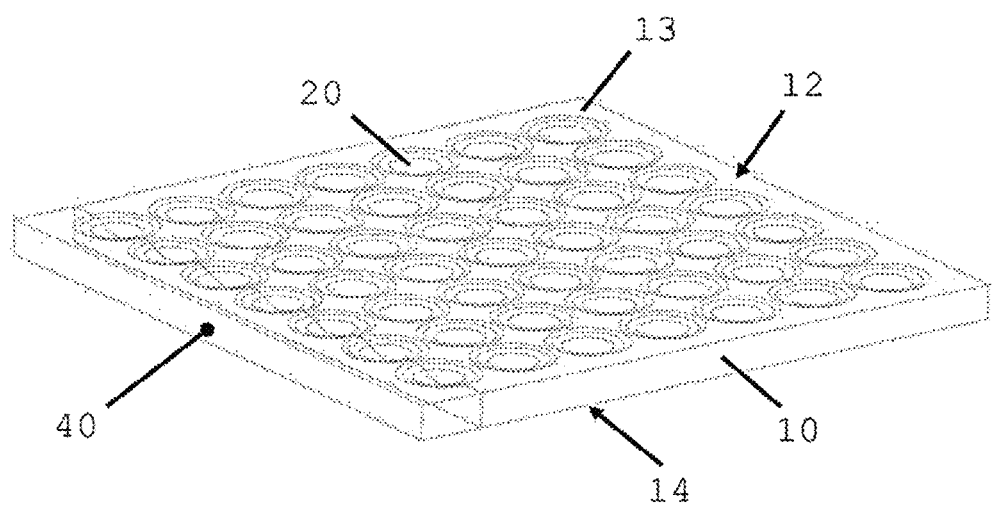
FIG. 4 shows an orthopedic device according to FIG. 3 with a vacuum applied.

In FIG. 4, the embodiment according to FIG. 3 is shown in a state in which a negative pressure has been applied by the suction port 40. The regions 20 provided with the adhesive coating are drawn into the recesses 30, such that a cup-like, indented surface structure is obtained. Beyond the plane formed by the non-adhesive or adhesion-reduced coating 13 in the region of the main body 10, the adhesive regions 20 are set back, and the second surface 14 has remained substantially flat.

Figure 5:
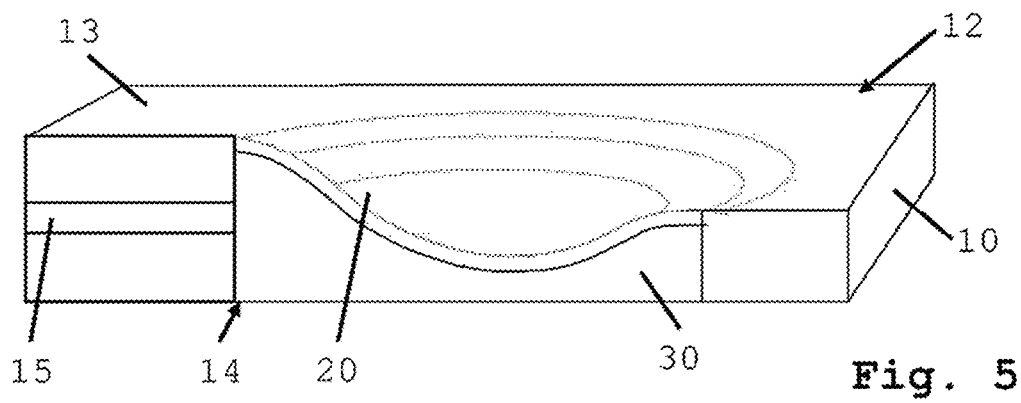
FIG. 5 shows a detail from FIG. 4 in an enlarged sectional view.

FIG. 5 shows a sectional view through a part of an orthopedic device 1 with the main body 10, the recess 30 formed thereon, and the first and second surfaces 12 and 14, which together with the main body 10 close off a volume which, by way of a connection channel 15, is fluidically connected to a further recess (not shown) and to a corresponding volume. In the state according to FIG. 5, the first surface 12 is drawn with the adhesive region 20 into the recess 30, since a negative pressure is applied within the recess 30. If a positive pressure is applied or the negative pressure is compensated, such that atmospheric pressure prevails inside the recess, the first surface 12 returns to its starting state, such that the adhesive region 20 lies in a plane with the rest of the first surface 12, in particular with the plane in which the non-adhesive coating 13 is applied. In the state shown, it is possible that the outside of the first surface 12 slides along a body bearing on it, since the non-adhesive or adhesion-reduced coating 13 allows this. As soon as the adhesive region 20 is pressed out in the plane of the non-adhesive coating 13 or in addition out of the recess 30, the adhesive region 20 comes into contact with the surface of the body bearing on it and increases the adhesion and reduces a relative movement between the orthopedic device and the further body.

The invention claimed is:

1. An orthopedic device, comprising:
a main body comprising at least one recess formed in the main body; and
a first surface comprising at least one adhesive region and at least one non-adhesive or adhesion-reduced region;
wherein said at least one recess overlaps the at least one adhesive region, the main body defines a pressure and/or suction port connected to the at least one recess, wherein the first surface is designed to be at least partially sucked into the at least one recess when a negative pressure is applied in the at least one recess and/or to be pushed out when a positive pressure is applied, wherein, when no pressure is applied to the at least one recess, the at least one adhesive region and the at least one non-adhesive or adhesion-reduced region is positioned in a starting plane that is configured to contact a body of a user, and wherein, when the negative pressure is applied to the at least one recess, the at least one adhesive region is positioned in a position which is deeper than the starting plane within the at least one recess such that the at least one adhesive region does not contact the body of the user and the at least one non-adhesive or adhesion-reduced region remains in the starting plane and remains in contact with the body of the user.

2. The orthopedic device of claim 1, wherein the first surface is formed separately from the main body and is secured thereon.

3. The orthopedic device of claim 1, wherein on a side of the main body lying opposite the first surface, a second, separate surface is secured which at least covers the at least one recess.

4. The orthopedic device of claim 1, wherein the entire first surface is designed to be adhesive, or wherein a coating for increasing or reducing the adhesion is applied to some regions of the first surface.

5. The orthopedic device of claim 4, wherein the at least one adhesive region is arranged exclusively above the at least one recess.

6. The orthopedic device of claim 1, wherein the first surface comprises a plurality of cup-like or channel-shaped recesses arranged in the main body and are fluidically connected to the pressure and/or suction port.

7. The orthopedic device of claim 6, wherein at least two of the cup-like or channel-shaped recesses in the main body are fluidically connected to the pressure and/or suction port via a valve.

8. The orthopedic device of claim 1, wherein the first surface comprises a plurality of cup-like or channel-shaped recesses arranged in the main body and are fluidically connected to one another.

9. The orthopedic device of claim 8, wherein throttles or valves are arranged in the fluidic connections between the plurality of cup-like or channel-shaped recesses.

10. The orthopedic device of claim 1, wherein the at least one recess extends as far as an edge of the orthopedic device.

11. The orthopedic device of claim 1, wherein the first surface is produced from an elastic material.

12. The orthopedic device of claim 1, wherein the orthopedic device is designed as a cuff, prosthesis liner, prosthesis socket or prosthesis socket component.

13. The orthopedic device of claim 1, wherein the orthopedic device is designed as a prosthesis socket component and the prosthesis socket component has fastening devices for reversible fastening to a dimensionally stable outer socket.

14. An orthopedic device, the device comprising:
a main body comprising at least one recess formed in the main body;
a first surface comprising at least one adhesive region, the at least one recess overlapping the at least one adhesive region and at least one non-adhesive or adhesion-reduced region; and
a second surface substantially opposite the first surface and covering the at least one recess, wherein the main body defines a pressure and/or suction port connected to the at least one recess;
wherein the first surface is designed to be at least partially sucked into the at least one recess when a negative pressure is applied in the at least one recess and/or to be pushed out when a positive pressure is applied, wherein, when no pressure is applied to the at least one recess, the at least one adhesive region and the at least one non-adhesive or adhesion-reduced region is positioned in a starting plane that is configured to contact a body of a user, and wherein, when the negative pressure is applied to the at least one recess, the at least one adhesive region is positioned in a position which is deeper than the starting plane within the at least one recess such that the at least one adhesive region does not contact the body of the user and the at least one non-adhesive or adhesion-reduced region remains in the starting plane and remains in contact with the body of the user.

15. The orthopedic device of claim 14, wherein the entire first surface is designed to be adhesive.

16. The orthopedic device of claim 14, wherein the first surface comprises a plurality of cup-like or channel-shaped recesses arranged in the main body and are fluidically connected to the pressure and/or suction port.

17. The orthopedic device of claim 16, wherein at least two of the cup-like or channel-shaped recesses are fluidically connected to the pressure and/or suction port via a valve.

18. The orthopedic device of claim 14, wherein the first surface comprises a plurality of cup-like or channel-shaped recesses arranged in the main body and are fluidically connected to one another.

19. An orthopedic device, the device comprising:
a main body with a first surface, the main body further comprising at least one recess at least overlapping at least one adhesive region formed on the first surface, at least one non-adhesive or adhesion-reduced region formed on the first surface, and a pressure and/or suction port, the main body further comprising:
a second surface substantially opposite the first surface; and
the first surface comprises a plurality of cup-like or channel-shaped recesses fluidically connected to the pressure and/or suction port;
wherein the first surface is designed to be at least partially sucked into the at least one recess when a negative pressure is applied in the at least one recess and/or to be pushed out when a positive pressure is applied, and wherein the second surface covers the at least one recess of the main body, wherein, when no pressure is applied to the at least one recess, the at least one adhesive region and the at least one non-adhesive or adhesion-reduced region is positioned in a starting plane that is configured to contact a body of a user, and wherein, when the negative pressure is applied to the at least one recess, the at least one adhesive region is positioned in a position which is deeper than the starting plane within the at least one recess such that the at least one adhesive region does not contact the body of the user and the at least one non-adhesive or adhesion-reduced region remains in the starting plane and remains in contact with the body of the user.

* * * * *